United States Patent
Lau et al.

(10) Patent No.: US 11,854,703 B2
(45) Date of Patent: Dec. 26, 2023

(54) SIMULATING ABNORMALITIES IN MEDICAL IMAGES WITH GENERATIVE ADVERSARIAL NETWORKS

(71) Applicant: ARTERYS INC., San Francisco, CA (US)

(72) Inventors: Hok Kan Lau, San Francisco, CA (US); Jesse Lieman-Sifry, San Francisco, CA (US); Sean Patrick Sall, San Francisco, CA (US); Berk Dell Norman, San Francisco, CA (US); Daniel Irving Golden, Palo Alto, CA (US); John Axerio-Cilies, Berkeley, CA (US); Matthew Joseph Didonato, Redwood City, CA (US)

(73) Assignee: ARTERYS INC., San Francisco, CA (US)

( * ) Notice: Subject to any disclaimer, the term of this patent is extended or adjusted under 35 U.S.C. 154(b) by 472 days.

(21) Appl. No.: 17/251,138

(22) PCT Filed: Jun. 10, 2019

(86) PCT No.: PCT/US2019/036391
§ 371 (c)(1),
(2) Date: Dec. 10, 2020

(87) PCT Pub. No.: WO2019/241155
PCT Pub. Date: Dec. 19, 2019

(65) Prior Publication Data
US 2021/0249142 A1    Aug. 12, 2021

Related U.S. Application Data

(60) Provisional application No. 62/683,461, filed on Jun. 11, 2018.

(51) Int. Cl.
*G16H 50/50* (2018.01)
*G06T 7/11* (2017.01)
(Continued)

(52) U.S. Cl.
CPC ............ *G16H 50/50* (2018.01); *G06N 3/045* (2023.01); *G06N 3/047* (2023.01); *G06N 3/048* (2023.01);
(Continued)

(58) Field of Classification Search
CPC ........ G16H 30/40; G16H 50/20; G16H 50/50; G06T 7/11; G06T 2207/10081;
(Continued)

(56) References Cited

U.S. PATENT DOCUMENTS 9,513,357 B2   12/2016  Hsiao et al.
10,117,597 B2  11/2018  Beckers et al.
(Continued)

FOREIGN PATENT DOCUMENTS

WO    2018140596 A2    8/2018
WO    2018204698 A1    11/2018
WO    2018222755 A1    12/2018

OTHER PUBLICATIONS

Shin et al., "Abnormal Colon Polyp Image Synthesis Using Conditional Adversarial Networks for Improved Detection Performance", IEEE Access, vol. 6, Sep. 30, 2018, pp. 56007-56017 (Year: 2018).*

(Continued)

*Primary Examiner* — Nay A Maung
*Assistant Examiner* — Jose M Torres
(74) *Attorney, Agent, or Firm* — Seed IP Law Group LLP

(57) ABSTRACT

Systems and methods for providing a novel framework to simulate the appearance of pathology on patients who otherwise lack that pathology. The systems and methods (Continued)

include a "simulator" that is a generative adversarial network (GAN). Rather than generating images from scratch, the systems and methods discussed herein simulate the addition of diseases-like appearance on existing scans of healthy patients. Focusing on simulating added abnormalities, as opposed to simulating an entire image, significantly reduces the difficulty of training GANs and produces results that more closely resemble actual, unmodified images. In at least some implementations, multiple GANs are used to simulate pathological tissues on scans of healthy patients to artificially increase the amount of available scans with abnormalities to address the issue of data imbalance with rare pathologies.

36 Claims, 8 Drawing Sheets

(51) Int. Cl.
| | | |
|---|---|---|
| G16H 50/20 | (2018.01) | |
| G16H 30/40 | (2018.01) | |
| G06N 3/045 | (2023.01) | |
| G06N 3/048 | (2023.01) | |
| G06N 3/047 | (2023.01) | |
| G06N 3/088 | (2023.01) | |

(52) U.S. Cl.
CPC ............... *G06N 3/088* (2013.01); *G06T 7/11* (2017.01); *G16H 30/40* (2018.01); *G16H 50/20* (2018.01); *G06T 2207/10081* (2013.01); *G06T 2207/10088* (2013.01); *G06T 2207/20081* (2013.01); *G06T 2207/20084* (2013.01); *G06T 2207/30048* (2013.01); *G06T 2207/30056* (2013.01); *G06T 2207/30064* (2013.01)

(58) Field of Classification Search
CPC . G06T 2207/10088; G06T 2207/20081; G06T 2207/20084; G06T 2207/30048; G06T 2207/30056; G06T 2207/30064; G06N 3/045; G06N 3/047; G06N 3/048; G06N 3/088
See application file for complete search history.

(56) References Cited

U.S. PATENT DOCUMENTS

| | | | |
|---|---|---|---|
| 10,331,852 B2 | 6/2019 | Dormer et al. | |
| 10,600,184 B2 | 3/2020 | Golden et al. | |
| 10,869,608 B2 | 12/2020 | Dormer et al. | |
| 10,871,536 B2 | 12/2020 | Golden et al. | |
| 10,902,598 B2 | 1/2021 | Golden et al. | |
| 2015/0238148 A1 | 8/2015 | Georgescu et al. | |
| 2018/0256042 A1 | 9/2018 | Beckers et al. | |
| 2018/0307947 A1* | 10/2018 | Choi | G06F 18/22 |
| 2018/0336439 A1* | 11/2018 | Kliger | G06N 3/047 |
| 2018/0336471 A1* | 11/2018 | Rezagholizadeh | G06N 3/047 |
| 2019/0066281 A1* | 2/2019 | Zheng | G06T 7/174 |
| 2019/0073770 A1* | 3/2019 | Moradi | G06N 3/045 |
| 2019/0197358 A1* | 6/2019 | Madani | G06N 3/045 |
| 2019/0252073 A1* | 8/2019 | Hsu | G06N 3/047 |
| 2020/0012904 A1* | 1/2020 | Zhao | G06N 3/084 |

OTHER PUBLICATIONS

Ben-Cohen et al., "Cross-Modality Synthesis from CT to PET using FCN and GAN Networks for Improved Automated Lesion Detection", arXiv:1802.07846, Jul. 24, 2018, pp. 1-9 (Year: 2018).*

Baur et al., "MelanoGANs: High Resolution Skin Lesion Synthesis with GANs," 2018, arXiv [cs.CV]. arXiv, http://arxiv.org/abs/1804.04338.

Bidulock et al., "Systems and Methods for Longitudinally Tracking Fully De-Identified Medical Studies," U.S. Appl. No. 62/589,766, filed Nov. 22, 2017, 136 pages.

Chuquicusma et al., "How to Fool Radiologists with Generative Adversarial Networks? A Visual Turing Test for Lung Cancer Diagnosis," 2018, In *2018 IEEE 15th International Symposium on Biomedical Imaging (ISBI 2018)*, pp. 240-244.

Costa et al.,. "Towards Adversarial Retinal Image Synthesis." Jan. 2017, arXiv [cs.CV], https://arxiv.org/abs/1701.08974.

De Francesco et al., "Medical Imaging, Efficient Sharing and Secure Handling of Medical Imaging Information," U.S. Appl. No. 62/501,613, filed May 30, 2017, 161 pages.

Duchateau et al., "Model-based generation of large databases of cardiac images: synthesis of pathological cine MR sequences from real healthy cases," IEEE Transactions on Medical Imaging, Institute of Electrical and Electronics Engineers, 2018, 37, pp. 755-766. 10.1109/TMI.2017.2714343. hal-01533788.

Esteva et al., "Dermatologist-Level Classification of Skin Cancer with Deep Neural Networks," 2017, Nature 542 (7639): 115-18.

Frid-Adar et al., "GAN-Based Synthetic Medical Image Augmentation for Increased CNN Performance in Liver Lesion Classification," 2018, arXiv [cs.CV]. arXiv. http://arxiv.org/abs/1803.01229.

Golden et al., "Autonomous Detection of Medical Study Types," U.S. Appl. No. 62/589,833, filed Nov. 22, 2017, 178 pages.

Golden et al., "Content Based Image Retrieval for Lesion Analysis," U.S. Appl. No. 62/589,805, filed Nov. 22, 2017. 189 pages.

Golden et al., "Patient Outcomes Prediction System," U.S. Appl. No. 62/589,838, filed Nov. 22, 2017, 187 pages.

Goodfellow et al., "Generative Adversarial Networks," 2014, arXiv [stat.ML]. arXiv. http://arxiv.org/abs/1406.2661.

Guibas et al., "Synthetic medical images from dual generative adversarial networks," 31st Conference on Neural Information Processing Systems, Long Beach, CA, USA, Jan. 8, 2018, pp. 1-9.

International Search Report and Written Opinion, dated Oct. 1, 2019, for International Patent Application No. PCT/US2019/036391. (14 pages).

Isola et al., "Image-to-Image Translation with Conditional Adversarial Networks," 2016, arXiv [cs.CV]. arXiv, http://arxiv.org/abs/1611.07004.

Kingma et al., "Adam: A Method for Stochastic Optimization," 2014, arXiv [cs.LG]. arXiv, http://arxiv.org/abs/1412.6980.

Lau et al., "ScarGAN: chained generative adversarial networks to simulate pathological tissue on cardiovascular MR scans," Arterys Inc., Aug. 14, 2018. (12 pages).

Lau et al., "Simulating Abnormalities in Medical Images With Generative Adversarial Networks," U.S. Appl. No. 62/683,461, filed Jun. 11, 2018, 39 pages.

Law et al., "Automated Three Dimensional Lesion Segmentation," U.S. Appl. No. 62/589,876, filed Nov. 22, 2017, 182 pages.

Leibowitz et al., "Systems and Methods for Interaction With Medical Image Data," U.S. Appl. No. 62/589,872, filed Nov. 22, 2017, 187 pages.

Lieman-Sifry et al., "Automated Lesion Detection, Segmentation, and Longitudinal Identification," U.S. Appl. No. 62/512,610, filed May 30, 2017, 87 pages.

Mao et al., "Least Squares Generative Adversarial Networks," 2016, arXiv [cs.CV]. arXiv, http://arxiv.org/abs/1611.04076.

Mariani et al., "BAGAN: Data Augmentation with Balancing GAN." 2018, arXiv [cs.CV]. arXiv, http://arxiv.org/abs/1803.09655.

Mirza et al., "Conditional Generative Adversarial Nets," 2014, arXiv [cs.LG]. arXiv, http://arxiv.org/abs/1411.1784.

Newton et al., "Three Dimensional Voxel Segment Tool," U.S. Appl. No. 62/589,772, filed Nov. 22, 2017, 180 pages.

Odena et al., "Conditional Image Synthesis With Auxiliary Classifier GANs," 2016, arXiv [stat.ML]. arXiv. http://arxiv.org/abs/1610.09585.

Radford et al., "Unsupervised Representation Learning with Deep Convolutional Generative Adversarial Networks," 2015, arXiv [cs.LG]. arXiv, http://arxiv.org/abs/1511.06434.

(56) References Cited

OTHER PUBLICATIONS

Salehinejad et al., "Generalization of Deep Neural Networks for Chest Pathology Classification in X-Rays Using Generative Adversarial Networks," 2017, *arXiv* [*cs.CV*]. arXiv, http://arxiv.org/abs/1712.01636.

Schulz-Menger et al., "Standardized image interpretation and post processing in cardiovascular magnetic resonance: society for cardiovascular magnetic resonance (SCMR) board of trustees task force on standardized post processing," *Journal of Cardiovascular Magnetic Resonance: Official Journal of the Society for Cardiovascular Magnetic Resonance* 15:35, May 2013.

Shrivastava et al., "Learning from Simulated and Unsupervised Images through Adversarial Training," 2016, *arXiv* [*cs.CV*]. arXiv, http://arxiv.org/abs/1612.07828.

Sixt et al., "RenderGAN: Generating Realistic Labeled Data," 2016, *arXiv* [*cs.NE*]. arXiv, http://arxiv.org/abs/1611.01331.

Taerum et al., "Automated Lesion Detection, Segmentation, and Longitudinal Identification," U.S. Appl. No. 62/589,825, filed Nov. 22, 2017, 192 pages.

Wolterink et al., "Deep MR to CT Synthesis Using Unpaired Data," 2017, *arXiv* [*cs.CV*]. arXiv, http://arxiv.org/abs/1708.01155.

Zhao et al., "Synthesizing Filamentary Structured Images with GANs," 2017, *arXiv* [*cs.CV*]. arXiv, http://arxiv.org/abs/1706.02185.

Zhu et al., "Unpaired Image-to-Image Translation Using Cycle-Consistent Adversarial Networks," 2017, *arXiv* [*cs.CV*]. arXiv, http://arxiv.org/abs/1703.10593.

Beckers et al., "Apparatus, Methods and Articles for Four Dimensional (4D) Flow Magnetic Resonance Imaging," U.S. Appl. No. 61/928,702, filed Jan. 17, 2014, 106 pages.

Beckers et al., "Medical Imaging and Efficient Sharing of Medical Imaging Information," U.S. Appl. No. 62/260,565, filed Nov. 29, 2015, 67 pages.

Dormer et al., "Medical Imaging and Efficient Sharing of Medical Imaging Information," U.S. Appl. No. 62/415,203, filed Oct. 31, 2016, 111 pages.

Golden et al., "Automated Cardiac Volume Segmentation," U.S. Appl. No. 62/415,666, filed Nov. 1, 2016, 85 pages.

Golden et al., "Automated Segmentation Utilizing Fully Convolutional Networks," U.S. Appl. No. 62/451,482, filed Jan. 27, 2017, 113 pages.

\* cited by examiner

SIMULATING ABNORMALITIES IN MEDICAL IMAGES WITH GENERATIVE ADVERSARIAL NETWORKS

BACKGROUND

Recently, deep learning has shown promising results to automate many tasks in radiology such as skin lesion classification[1]. The performance of these deep convolutional neural networks (DCNNs) is sometimes on par with clinicians but usually require a large amount of training images and labels. Training a DCNN that performs equally well across different patients is challenging because some pathologies and congenital diseases are rare and that leads to class imbalance. Without enough training data for rare pathologies, DCNNs might not perform well on these patients even though they are the ones that require the most clinical care and early detection of these diseases will be life-saving.

DESCRIPTION OF RELATED ART

The generative adversarial network (GAN) framework was first proposed by Goodfellow et al.[2] and consists of 2 networks: a generative network that transforms a noise vector into realistic samples, and a discriminator network that classifies samples as real or fake. The training process of these 2 networks is a minimax game because the objective of the generator is to "fool" discriminator. Radford et al.[3] propose Deep Convolutional Generative Adversarial Network (DCGAN) that uses deconvolutional layers in the generator to produce more realistic samples. More recently, pix2pix was proposed by Isola et al.[4] wherein a fully convolutional U-Net in the generator performs image translation; the generative network receives an image in one domain and outputs the corresponding image of another domain. Mao et al.[5] propose Least Squared Generative Adversarial Network (LSGAN) to address the vanishing gradients problem when optimizing GANs.

Previous work has used GANs to refine the results of a simulator. Sixt et al.[6] propose RenderGAN in which the generator outputs simulator parameters and other details to be added to the simulated samples. Shrivastava et al.[7] propose SimGAN in which the generator refines the output of a simulator. Mariani et al.[8] propose BAGAN to address data imbalance by generating samples of rare classes. Mirza et al.[9] propose Conditional Adversarial Network and later Odena et al.[10] propose ACGAN to generate samples of a specific class.

GANs have been also used in medical imaging for data augmentation. Costa et al.[11] and Zhao et al.[12] use pix2pix to generate retinal images from the vessel segmentation mask. Synthetic training samples (such as skin lesions[13], liver lesions[14] and lung nodules[15]) are generated by GAN to increase the size of the training dataset or as education purposes for radiologists. GANs are also being used to help segmentation networks to work well across different modalities, with CycleGAN proposed by Zhu et al.[16] segmenting brain images in both computed tomography (CT) and magnetic resonance (MR)[17]. Salehinej ad et al.[18] use DCGAN to synthesize X-ray chest scans with under-represented diseases and to classify lung diseases.

BRIEF SUMMARY

A machine learning system may be summarized as including at least one nontransitory processor-readable storage medium that stores at least one of processor-executable instructions or data; and at least one processor communicably coupled to the at least one nontransitory processor-readable storage medium, in operation, the at least one processor: receives learning data comprising a plurality of batches of labeled image sets and corresponding segmentation masks, each image set comprising image data representative of an input anatomical structure; simulates abnormalities on at least some of the images and their corresponding segmentation masks without abnormalities using a plurality of trained convolutional neural network (CNN) models stored on the at least one nontransitory processor-readable storage medium; and stores the simulated abnormalities as images and corresponding segmentation masks in the at least one nontransitory processor-readable storage medium of the machine learning system. At least some of the images may include abnormalities including the simulated abnormalities or real abnormalities.

The abnormalities may be in cardiac images, and include one or more of myocardial scarring, myocardial infarction, coronary stenosis, or perfusion characteristics of the cardiac myocardium. The abnormalities may be in lung images, and include one or more of ground glass, solid lung nodules, or sub-solid lung nodules. The abnormalities may be in liver images, and include one or more of Hemangiomas, Focal Nodular Hyperplasias lesions, Hepatocelualar Adenomas lesions, or cystic masses. The CNN models may include a discriminator which receives learning data including a plurality of batches of real samples and simulated samples and classifies if the samples contain real abnormalities, simulated abnormalities or no abnormalities.

The discriminator may be a mask discriminator, and the learning data may include segmentation masks with real abnormalities and segmentation masks with simulated abnormalities from a mask generator. The discriminator may be a refining discriminator, and the learning data may include images without abnormalities and images with simulated abnormalities from a refining generator. The learning data may include past simulated samples from a refining generator or a mask generator.

At least one storage device with a fixed capacity may store past simulated images and segmentation masks from the mask generator and the refining generator. If the storage device is out of capacity, at least one random simulated image or segmentation mask may be removed to accommodate new inputs. The CNN models may include a discriminator including at least one group of layers that includes at least one convolution layer, max pooling layer, batch normalization layer and dropout layer where a nonlinearity including rectifier or leaky rectifier is applied after each multiplication, wherein there are more than one residual connection and skip connection among the group, and one output layer that includes at least one neuron. The output layer may contain at least one neuron with a nonlinearity applied. The nonlinearity may include softmax. The CNN models may include a discriminator that is optimized using stochastic gradient descent using at least one differentiable objective function that is indicative of the accuracy of the discriminator.

A differentiable objective function may include a combination of mean squared error, categorical cross-entropy or Wasserstein distance. A differentiable objective function may include a classification loss including categorical cross-entropy between the predicted and ground truth abnormality features.

The CNN models may include a mask discriminator and a mask generator, and the mask generator which receives learning data comprising a plurality of batches of real segmentation masks to add simulated abnormal tissues to the segmentation masks. The mask generator may include a contracting path and an expanding path, the contracting path may include a number of convolutional layers and a number of pooling layers, each pooling layer preceded by at least one convolutional layer, and the expanding path may include a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation. The CNN models may include a mask discriminator and a mask generator, and the mask generator and the mask discriminator may be optimized together with stochastic gradient descent such that the simulated segmentation mask generated by the mask generator maximizes the error of the mask discriminator and minimizes the differences between the input and output segmentation masks using at least one differentiable objective functions.

The differentiable objective function that maximizes the error of the mask discriminator may include at least mean squared error or Wasserstein distance. The differentiable objective function that minimizes the differences between the input and output images may include at least one of mean absolute error, mean squared error, or categorical cross-entropy. The mask generator may be optimized for N gradient steps and the mask discriminator may be optimized for M gradients steps, where N and M are positive integers. N and M may be different positive integers. N and M may be equal to each other. The at least one processor may apply the simulated segmentation mask with simulated abnormalities to the images by changing the intensity values of the corresponding pixels which belong to the simulated abnormalities. The at least one processor may calculate the average intensity of abnormalities in the learning data and apply the calculated average intensity to the image to the pixels of the image which belong to the simulated abnormalities. The at least one processor may uniformly sample from anatomical structures in the image and apply the sampled intensities of the image to the pixels of the image which belong to the simulated abnormalities. Anatomical structures that the at least one processor sampled from may include the left endocardium of heart images.

The CNN models may include a mask generator, a mask discriminator, and a refining generator, and the refining generator may receive learning data including a plurality of batches of real images, segmentation masks with simulated abnormalities from the mask generator, and produces simulated abnormalities on the image using the received learning data. The refining generator may include a contracting path and an expanding path, the contracting path may include a number of convolutional layers and a number of pooling layers, each pooling layer preceded by at least one convolutional layer, and the expanding path may include a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation.

The CNN models may include a refining discriminator, and the refining generator and the refining discriminator may be optimized together with stochastic gradient descent using at least one differentiable objective function such that the refining generator maximizes the error of the refining discriminator and minimizes the differences between the input and output images. The differentiable objective function that maximizes the error of the refining discriminator may include a combination of mean squared error or categorical cross-entropy. The differentiable objective function that minimizes the differences between the input and output image may include at least one of mean absolute error or mean squared error. The mask generator may be optimized for N gradient steps and the mask discriminator may be optimized for M gradients steps where N and M are positive integers. N and M may be different positive integers. N and M may be equal to each other.

The image data may be representative of a chest, including lungs and heart, or of an abdomen, including a liver. The image data may include computed tomography (CT) scan data or magnetic resonance (MR) scan data. The image data may be captured at any of a plurality of acquisition angles including short-axis of the heart, long-axis of the heart, axially, sagittally, or coronally.

A machine learning system may be summarized as including at least one nontransitory processor-readable storage medium that stores at least one of processor-executable instructions or data; and at least one processor communicably coupled to the at least one nontransitory processor-readable storage medium, in operation, the at least one processor: receives learning data comprising a plurality of batches of labeled image sets and corresponding segmentation masks, each image set comprising image data representative of an input anatomical structure; trains a segmentation network to segment anatomical structure using the received learning data, the segmentation network comprising one or more CNN models; trains a classification network to classify abnormalities using the received learning data, the classification network comprising one or more CNN models; and stores the trained segmentation network and the trained classification network in at least one nontransitory processor-readable storage medium.

The segmentation network may receive learning data including a plurality of batches of training images and training segmentation masks with and without abnormalities. At least some of the learning images may include cardiac images, and the abnormalities may include one or more of myocardial scarring, myocardial infarction, coronary stenosis, or perfusion characteristics of the cardiac myocardium. At least some of the training images may include lung images, and the abnormalities may include one or more of ground glass, solid lung nodules, or sub-solid lung nodules. At least some of the training images may include liver images, and the abnormalities may include one or more of Hemangiomas, Focal Nodular Hyperplasias lesions, Hepatocellualar Adenomas lesions, or cystic masses.

The training images may include real images with and without abnormalities. The training images may include images with simulated abnormalities. Images with simulated abnormalities may be generated by a refining generator. Ground truth segmentation masks may represent anatomical structures. Ground truth segmentation masks may represent simulated and real abnormalities. Segmentation masks with simulated abnormalities may be generated by a mask generator.

The CNN models may predict segmentation masks of left and right endocardium and epicardium in heart images. The CNN models may predict segmentation masks of lung nodules in lung images. The CNN models may predict segmentation masks of liver lesions in liver images. The CNN models may include a contracting path and an expanding path, the contracting path may include a number of convolutional layers and a number of pooling layers, each pooling layer preceded by at least one convolutional layer, and the expanding path may include a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation.

The classification network may receive learning data including a plurality of batches of training images and training labels with and without abnormalities. At least some of the training images may include cardiac images, and the abnormalities may include one or more of myocardial scarring, myocardial infarction, coronary stenosis, or perfusion characteristics of the cardiac myocardium. At least some of the training images may include lung images, and the abnormalities may include one or more of ground glass, solid and sub-solid lung nodules. At least some of the training images may include liver images, and the abnormalities may include one or more of Hemangiomas, Focal Nodular Hyperplasias lesions, Hepatocellualar Adenomas lesions, or cystic masses.

The training images may include real images with and without abnormalities. The training images may include images with simulated abnormalities. Images with simulated abnormalities may be generated by one or more generators.

The CNN models may predict the type of abnormalities in heart images. The CNN models may predict the type of abnormalities in lung images. The CNN models may predict the type of abnormalities in liver images. The classification network may include at least one group of layers that includes at least one convolution layer, max pooling layer, batch normalization layer and dropout layer where a nonlinearity including rectifier and leaky rectifier is applied after each multiplication, wherein there are more than one residual connection and skip connections among the group, and one output layer that includes at least one neuron with optionally a nonlinearity applied including softmax.

The at least one processor may optimize the CNN models using stochastic gradient descent using at least one differentiable objective function indicative of the accuracy of the CNN models. The differentiable objective function may include per-pixel categorical cross-entropy or dice coefficient between the predicted and ground truth segmentation masks. The differentiable objective function may include categorical cross-entropy between the predicted and ground truth class probabilities of labels including abnormality types. The differentiable objective function may include mean squared error or mean absolute error of the predicted and ground truth abnormality measurements and severities. The differentiable objective function may be weighted such that a certain area of the mask including abnormalities is scaled by a scaling factor. For each CNN model, the at least one processor may fine tune the CNN model on data of the same type for which the CNN model will be used for inference. For each CNN model, to fine tune the CNN model, the at least one processor may retrain some or all of the layers of the CNN model.

The at least one processor may segment anatomical structure using the segmentation network; classify abnormalities using the classification network; and store the segmented anatomical structure and classified abnormalities in the at least one nontransitory processor-readable storage medium.

One or more implementations may include a method of operating a machine learning system as discussed herein.

DETAILED DESCRIPTION

Figure 1:
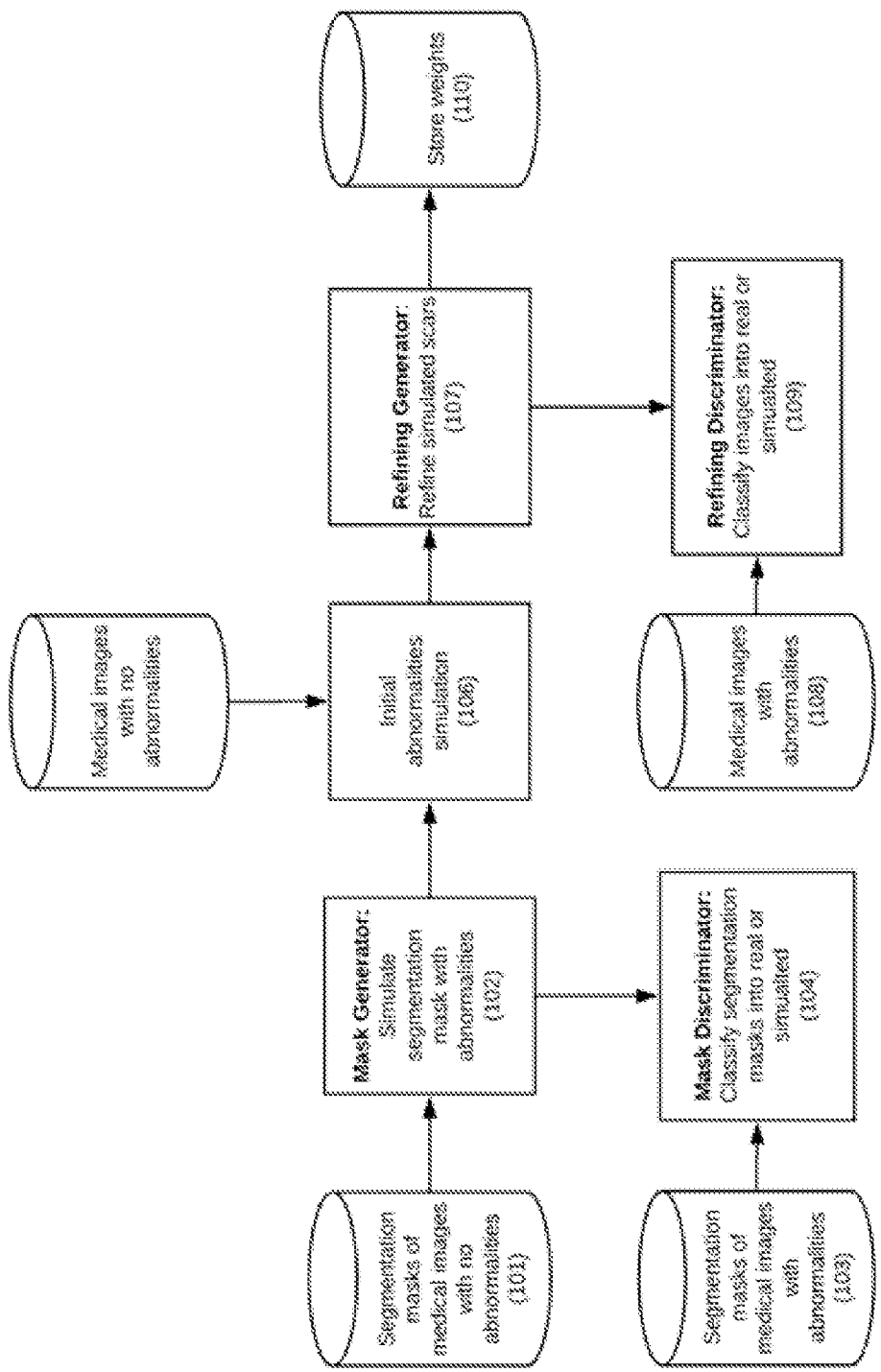
FIG. 1 shows a diagram of training an AbnormalGAN system to simulate abnormalities on scans without abnormalities.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

First Embodiment Description: Generative Adversarial Networks to Simulate Abnormalities We have developed a novel framework, which we name AbnormalGAN, to simulate the appearance of pathology on patients who otherwise lack that pathology. AbnormalGAN is similar to SimGAN, except that the "simulator" in AbnormalGAN is also a GAN and that manual modelling of abnormalities is not required. The motivation of the work from Salehinej ad et al. is similar to ours but instead of generating images from scratch, AbnormalGAN simulates the addition of diseases-like appearance on existing scans of healthy patients. This difference is important as focusing on simulating added abnormalities, as opposed to simulating an entire image, significantly reduces the difficulty of training GANs and produces results that more closely resemble actual, unmodified images.

We propose AbnormalGAN, where we use multiple generative adversarial networks (GAN) to simulate pathological tissues on scans of healthy patients to artificially increase the amount of available scans with abnormalities to address the issue of data imbalance with rare pathologies.

In the first stage, AbnormalGAN uses a mask generator to simulate the shape of the abnormalities given an input segmentation mask of certain anatomical structures. Abnormalities may include cardiac pathologies, such as any of myocardial scarring, myocardial infarction, coronary stenosis, or perfusion characteristics of the cardiac myocardium in cardiac images; ground glass, solid and sub-solid lung nodules in lung images. Abnormalities may also include Hemangiomas, Focal Nodular Hyperplasias and Hepatocelluaar Adenomas lesions and cystic masses in liver images. Other abnormalities in other disease and organ images are also possible.

In the second stage, we apply the shape of the simulated abnormalities to the image using a heuristic-based method.

In the final stage, AbnormalGAN uses a refining network to add details to the initial simulation from the heuristic-based method above.

First Embodiment Operation: Generative Adversarial Networks to Simulate Abnormalities FIG. 1 shows diagram of training AbnormalGAN system to simulate abnormalities on scans without abnormalities.

Training of AbnormalGAN has three main processes:
1. Training a mask generator to generate the shape of the abnormalities given an input segmentation mask of anatomical structures (102 and 104);
2. Applying a domain-specific heuristic to apply the shape of the simulated abnormalities to the image (106);
3. Training a refining generator to refine the initial simulation to provide realistic-looking abnormalities (107 and 108).

Simulating Segmentation Masks with Abnormalities and Classifying Segmentation Masks into Real or Simulated Masks (102 and 104)

Segmentation masks with simulated abnormalities (102) are generated by a mask generator network. Classification of segmentation masks into real or simulated masks (104) is performed by a mask discriminator network.

Inputs of the mask generator include a segmentation mask of the abnormalities (101). Outputs of the mask generator include a segmentation mask that includes simulated abnormalities and segmentation mask of the abnormalities. The reason why both the input and output include the segmentation mask of anatomical structures is to encourage the mask generator to learn the anatomical structures of the images before the mask discriminator gets too strong which will destabilize training. We apply output nonlinearity including softmax to convert into probabilities from 0 to 1.

In at least some embodiments, the mask generator is a fully convolutional segmentation network. A version of such mask generator includes 64 initial convolutional filters and skip connections between the corresponding downsampling and upsampling layers. At least some embodiments downsample using strides in the convolutional layers and there is one each of a convolutional layer, a batch normalization layer and a ReLU nonlinearity layer before each downsampling or upsampling operation. In at least some embodiments, we add noise to the generator by including dropout layers (p=0.25) after each nonlinearity layer.

The input of the mask discriminator includes a segmentation mask with real abnormalities (103) or a mask with simulated abnormalities (102). The output includes classification of whether the input is real or simulated and classification of abnormalities features including the type of scar in heart images, the type of nodules in lung images and the type of liver lesions in liver images.

The mask discriminator is a classification network. A version of such mask discriminator includes 4 layer blocks, each contains a convolutional layer, a batch normalization layer, and a leaky ReLU nonlinearity layer. The discriminator downsamples by using strides in its convolutional layers. In at least some other embodiments, the discriminator downsamples by using max-pooling layers.

Mask generator and mask discriminator are optimized together with stochastic gradient descent such that the simulated segmentation mask generated by the mask generator maximizes the error of the mask discriminator and minimize the differences between the input and output segmentation masks using at least one differentiable objective functions.

One version of training objective uses squared error as the main loss function. Thus the mask discriminator has no nonlinearity in its last layer. To regularize the mask generator, at least some embodiments add additional terms including multi-class cross-entropy between the input and output segmentation masks to encourage the network to produce realistic masks. In one version, the mask discriminator can be supervised by the features of the abnormalities using categorical cross-entropy and mean squared error. In at least one embodiment of the training process, we train the mask discriminator for 2 gradient steps for every gradient step performed on the mask generator.

In at least some embodiments, to prevent mode collapse, some of the simulated masks are stored in a buffer for "experience replay" such that the discriminators receive some training data from the experience replay buffer. In at least some embodiments, the discriminator receives half of the training data from the experience replay buffer. If the buffer that stores simulated masks exceeds its capacity, some past samples are randomly chosen and removed. The previously simulated samples stabilize training for both the discriminator and generator and prevent the generator from exploiting the discriminator by generating abnormalities of one specific shape which the discriminator has "forgotten."

In at least some embodiments, mode collapse is alleviated by injecting noise and conditioning the input by a noise vector. In at least one embodiment, we inject noise by using dropout at inference time so that the mask generator is not deterministic. In another version, we condition the mask generator by sampling a 192-d noise vector from a Gaussian distribution and duplicate it 192 times resulting in a 192× 192 2D image. The noise image is then stacked with the segmentation mask as inputs to the mask generator.

Heuristic for Initial Simulation (106)

Given an abnormality mask, one possible heuristic to generate abnormalities is to replace the corresponding pixels within the region of the abnormality mask with pixels for which the intensity is at the n-th percentile of intensity within normal tissues. For embodiments that are focused on cardiac studies, another possible heuristic is to replace the corresponding pixels within abnormalities by sampling from the intensities inside left ventricle (LV) endocardium (endo). However, LV segmentation also includes papillary muscles which are not hyperintense and have similar intensities as the myocardium (as they are both muscles). Therefore randomly sampling from such a distribution will result in salt-and-pepper-like noise in the abnormalities. To smooth out the noise, we can apply Gaussian blur on the simulated abnormalities.

In at least some embodiments, pixels within the region of simulated abnormalities are replaced by the 10th percentile intensity of normal tissues to provide initial abnormalities simulation.

Refining Image with Simulated Abnormalities and Classifying Images into Real or Simulated Masks (107 and 109)

Refined images with simulated abnormalities (107) are generated by a refining generator network. Classification of images into real or simulated masks (109) is performed by a refining discriminator network.

The input of the refining generator includes an image with simulated abnormalities from a heuristic-based method and the output of the refining generator includes the refined image with simulated abnormalities.

In at least some embodiments, the refining generator is a fully convolutional segmentation network. A version of such refining generator includes 64 initial convolutional filters and skip connections between the corresponding downsampling and upsampling layers. In some embodiments, the refining generator downsamples using strides in the convolutional layers and there is one each of a convolutional layer, a batch normalization layer and a ReLU nonlinearity layer before each downsampling or upsampling operation. In some embodiments, we add noise to the refining generator by using dropout layers (p=0.25) after each nonlinearity layer.

The input of the refining discriminator includes an image with abnormalities simulated by a heuristic method (106), images with real abnormalities (108). The output includes classification of whether the input is real or simulated and classification of abnormalities features including the type of scar in heart images, the type of nodules in lung images and the type of liver lesions in liver images.

The refining discriminator is a classification network. A version of refining discriminator includes 4 layer blocks, each contains a convolutional layer, a batch normalization layer, and a leaky ReLU nonlinearity layer. The refining discriminator also downsamples by using strides in its convolutional layers. In at least some other embodiments, the refining discriminator downsamples by using max-pooling layers.

One version of training objective uses squared error as the main loss function. Thus the refining discriminator has no nonlinearity in its last layer. To regularize the refining generator, we can add additional terms including absolute error between the input and the refined image, which encourages the refining generator to modify the intensities of small regions of the image. In one version, the refining discriminator can be supervised by the features of the abnormalities using categorical cross-entropy and mean squared error. In at least some embodiments, we train the refining discriminator for 3 gradient steps for every 1 gradient weight update to the refining generator.

We note that the weight of regularization in the training loss is a very important hyperparameter as it controls how similar the refined image should be with the input image. If it is too high, the refining network will be unable to change much of the image; if it is too low, the network might produce artifacts outside the myocardium to exploit the refining discriminator. In at least some embodiments, the optimization process includes performing a hyperparameter search on this regularization hypermeter.

In at least some embodiments, to prevent mode collapse, some of the simulated masks are stored in a buffer for "experience replay". If the buffer that stores simulated image exceeds its capacity, some past samples are randomly chosen and removed. The previously simulated samples stabilize training for both the refining discriminator and the refining generator and prevent the refining generator from exploiting the refining discriminator by generating abnormalities of one specific shape which the refining discriminator has "forgotten."

In at least some embodiments, mode collapse is alleviated by injecting noise and conditioning the input by a noise vector. In at least one embodiment, we inject noise by using dropout at inference time so that refining generator is not deterministic. In another version, we condition the refining generator by sampling a 192-d noise vector from a Gaussian distribution and duplicate it 192 times resulting in a 192× 192 2D image. The noise image is then stacked with the input image as inputs to refining generator.

Storing Weights of Trained Networks (110)

Weights of the trained networks can be stored in storage devices including hard disks and solid state drives to be used later for simulating abnormalities on scans without abnormalities.

Figure 2:
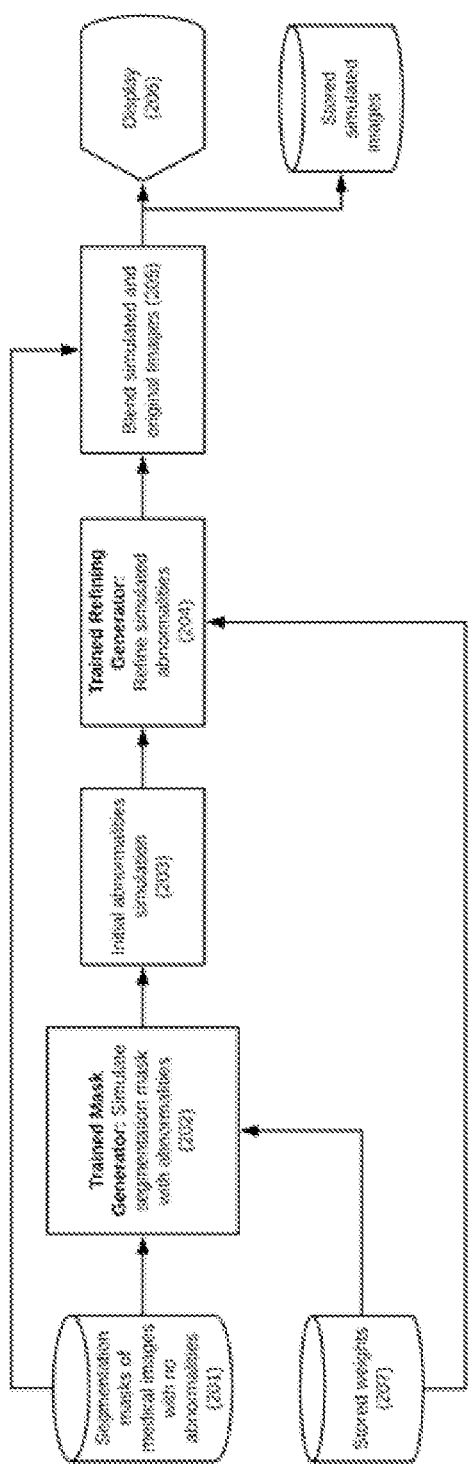
FIG. 2 shows a diagram of using a trained AbnormalGAN system to simulate abnormalities on scans without abnormalities

FIG. 2 shows a diagram of using a trained AbnormalGAN system to simulate abnormalities on scans without abnormalities.

Simulating abnormalities on scans without abnormalities using a trained AbnormalGAN system include three main processes:
  Using the mask generator with trained weights to generate the shape of the abnormalities given an input segmentation mask of anatomical structures (202);
  Applying a domain-specific heuristic to apply the shape of the simulated abnormalities to the image (203);
  Using a refining generator to refine the initial simulation to provide realistic-looking abnormalities (204);
  Blending simulated and original images (205).

Simulating Abnormalities with Trained Mask Generator, Heuristic and Trained Refining Generator (202, 203, 204)

To generate segmentation masks with abnormalities, segmentation masks of anatomical structures (201) are used as input for a trained mask generator. Sources of input anatomical structures segmentation masks include contours drawn by users or contours predicted by a trained segmentation network. Trained weights of a mask generator are retrieved from a storage device (207). The heuristic-based method described in (106) can be applied to provide initial abnormalities simulation. To refine the initial simulated abnormalities from (205), the initial simulation is used as inputs to a trained refining generator network. Trained weights of a refining generator are retrieved from a storage device, such as a hard disk or a solid state drive (207).

Blending Simulated and Original Images (205)

In at least some embodiments, a final post-processing step for the simulated image includes using a blending weight map to combine the refined image from the refining generator and the original image. This step removes any artifacts created by the refining generator outside the certain anatomical structures where abnormalities are unlikely to be located. In late-gadolinium enhancements (LGE) scans, scars can be confined in the left myocardium as scars do not locate outside the myocardium. We initialize the blending weight map as the myocardium mask and then apply Gaussian blur to the blending map to account for potentially inaccurate inputs contours. The final image with simulated abnormalities can be created by computing a per-pixel weighted average between the refined image from refining generator and the original image using the blending weight map.

The final image with simulated abnormalities can be displayed to a computer display (206) and saved to a storage device containing scans with simulated abnormalities.

Figure 3:
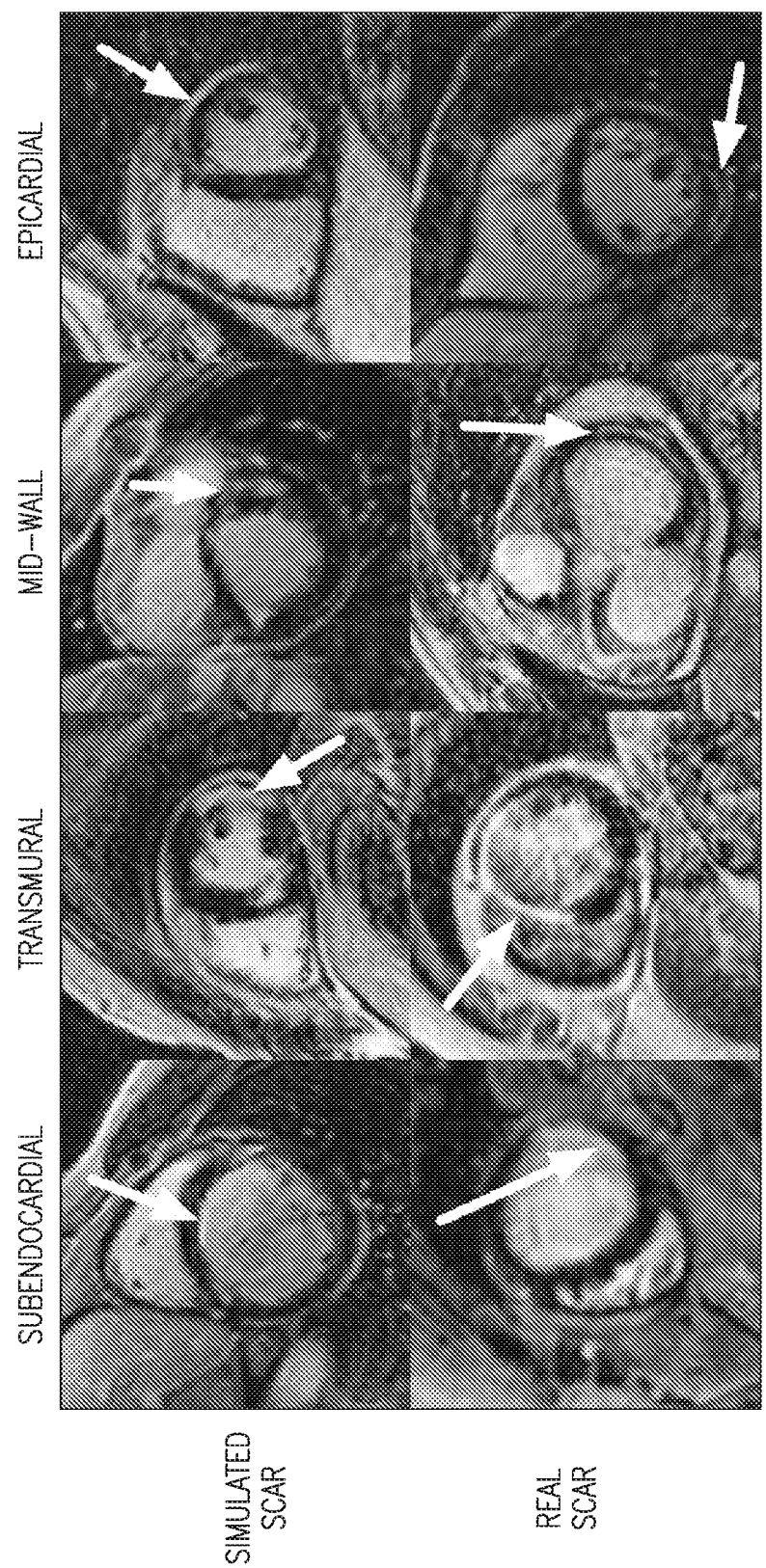
FIG. 3 shows samples of real and simulated scars on LGE scans categorized by enhancement patterns, with arrows indicating the locations of real or simulated scars.

FIG. 3 shows samples of real and simulated scars on LGE scans categorized by enhancement patterns. Arrows indicate the locations of real or simulated scars.

Figure 4:
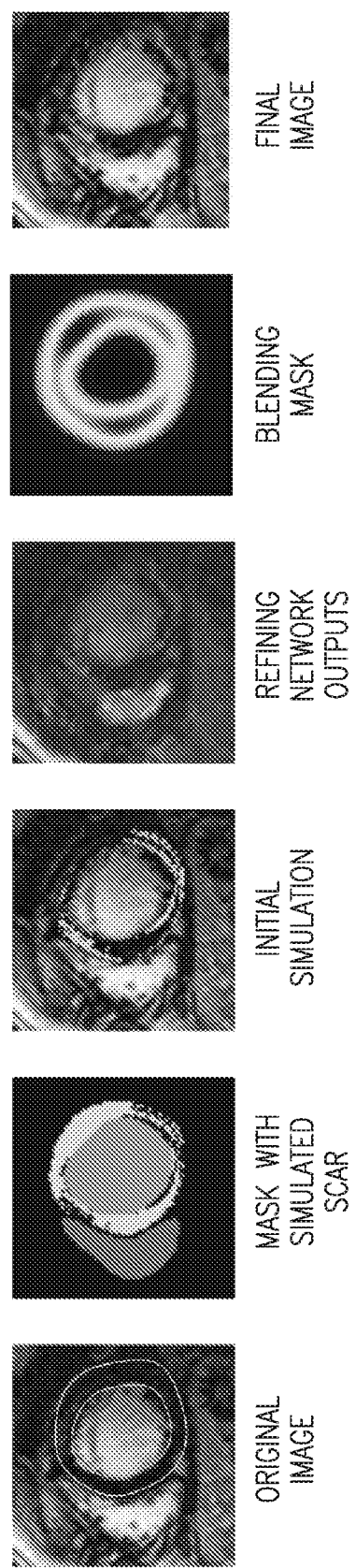
FIG. 4 shows, from left to right: an image with no scars and its right ventricle (RV) endo, LV epi, LV endo contours; simulated scars; heuristic-based simulation; output from refiner; blending mask; and final simulated image.

FIG. 4 shows, from left to right: image with no scars and its right ventricle (RV) endo, LV epi, LV endo contours; simulated scars (202); heuristic-based simulation (203); output from refiner (204); blending mask (205); final simulated image

Second Embodiment Description: Training Deep Convolutional Network Using Simulated Abnormalities In many medical datasets, images of patients with abnormalities comprise a relatively lower proportion of the dataset than images of normal patients. This leads to dataset imbalance, which can cause segmentation and classification accuracy to be lower for abnormal cases that those in normal cases. For patients with abnormalities, classification networks might have low accuracy including low recall and low precision. Segmentation networks might also predict segmentation masks that have low overlap with ground truth.

Deep convolutional networks including classification and segmentation networks can be trained with images with simulated abnormalities in conjunction with images with and without real abnormalities. Simulated abnormalities can address data imbalance by simulating abnormalities on healthy patients such that the proportion of images with abnormalities can be increased.

Training images are then stored in a database and classification or segmentation networks receive batches of images from such storage devices. Information retrieved from such storage devices includes image, labels and segmentation masks. DCNNs can be optimized using stochastic gradient descent method such as Adam[19] with differentiable objective function indicative of the accuracy of such network.

Weights of the trained network can be stored on a storage device including a hard drive, for example, and inference can then be performed to generate automated classification and segmentation of anatomical structures including abnormalities on otherwise unlabeled medical images.

Figure 5:
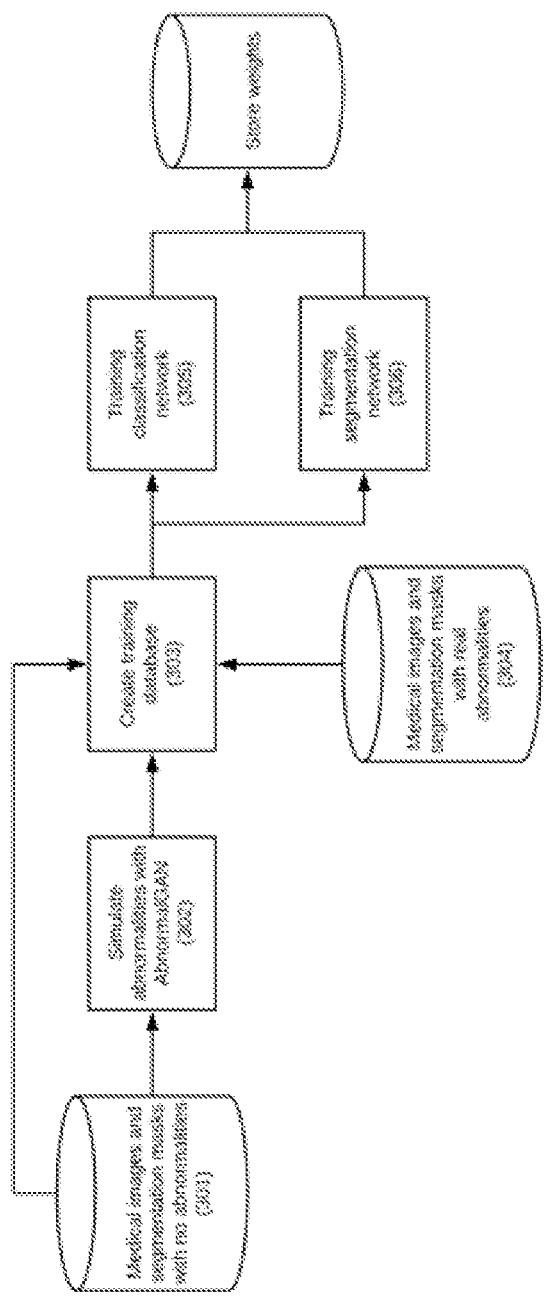
FIG. 5 shows training classification and segmentation networks using simulated abnormalities.

Second Embodiment Operation: Training Deep Convolutional Network Using Simulated Abnormalities FIG. 5 shows training classification and segmentation networks using simulated abnormalities.

Simulating Abnormalities with AbnormalGAN (302)

Simulation of abnormalities can be applied to medical images with no abnormalities (301). One or more mask generators and refining generators can be used to simulated abnormalities (203) to the same image.

To generate abnormalities of diverse shape, in at least some embodiments, we snapshot the weights of mask generators for every 10,000 training steps. We pick 5 of these snapshots by visually inspecting the shape of some of the simulated scars. These weight snapshots are selected if scars have relatively diverse shapes within the training set and across the weights snapshots. The number of training steps and number of snapshots may be varied in other embodiments.

Creating Training Database (303)

The training database includes normalized images, corresponding segmentation masks and labels. In at least some embodiments, the normalization process includes one or more of: resizing to a certain fixed image size, applying intensity normalization, enhancing contrast of certain parts of the images where structures are difficult to delineate. The training database can include images, masks and labels from different sources including images with real abnormalities (304), images with no abnormalities (301) and images with simulated abnormalities by AbnormalGAN (302).

Training Classification Network (305)

One version of classification network classification includes at least one group of layers that includes at least one convolution layer, max pooling layer, batch normalization layer and dropout layer where a nonlinearity such as a rectifier or leaky rectifier is applied after each multiplication, wherein there are more than one residual connection and skip connections among the group, and one output layer that includes at least one neuron with optionally a nonlinearity applied including softmax.

The classification network receives training samples including images and labels from the training database (303) including images with real abnormalities, images with no abnormalities, and images with simulated abnormalities from AbnormalGAN. A classification network is optimized using stochastic gradient descent using at least one differentiable objective function indicative of the accuracy of the classification network such as categorical cross-entropy between the predicted and ground truth class probabilities of labels including abnormality types or mean squared error and mean absolute error of the predicted and ground truth abnormality measurements and severities.

The weights of a trained classification network can be stored on a storage device, such as a hard disk or solid-state drive. The weights can be chosen by evaluation metrics on a set of held-out dataset that is indicative of the performance of a classification network on unseen images. Examples of evaluation metrics include categorical cross-entropy, per-class accuracy, precision, recall, and F1 scores. Training can be stopped if such evaluation metric stops improving.

Training Segmentation Network (306)

One version of segmentation network classification comprises of a contracting path and an expanding path, the contracting path includes a number of convolutional layers and a number of pooling layers, each pooling layer preceded by at least one convolutional layer, and the expanding path includes a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation.

Segmentation network receives training samples including images and masks from the training database (303) including images with real abnormalities, images with no abnormalities and images with simulated abnormalities from AbnormalGAN. A segmentation network is optimized using stochastic gradient descent using at least one differentiable objective function indicative of the accuracy of the segmentation network, such as per-pixel categorical cross-entropy or dice coefficient between the predicted and ground truth segmentation mask.

A Segmentation network can be pre-trained on a dataset on different modalities. In at least one embodiment, a network that segments LV endo, LV epicardium (epi) and RV endo on LGE scans can be pre-trained on steady-state free precession (SSFP) scans. Although LGE and SSFP are different types of MR acquisition, most parts of the ventricles have similar appearances where the blood pools appear brighter than surrounding muscles such as the myocardium. We note that scars are not visible in SSFP scans as SSFP does not use any contrast agents. Thus the network must learn all knowledge about scars from the LGE dataset.

The segmentation network can be modified to focus on the abnormalities. In one version, a network that segments LV endo, LV epi and RV endo on LGE scans can also predict as an auxiliary task the ground truth scar mask; in that case, the ground truth scar mask may be derived from a heuristic method, such as the full-width half-maximum method[20], from an explicit segmentation of the scar, or from the simulated scar mask. We can also modify the loss function to put stronger emphasis on scars such that a higher weighting is assigned to the corresponding pixels within scars. We note that this weighting is an important hyperparameter—if it is too high, the network will overestimate the amount of scars by erroneously including blood pool as part of the myocardium; if it is too low, the amount of scars will be underestimated by erroneously missing scars in the myocardium.

Automated Classification of Images with Unknown Abnormalities (400)

Figure 6:
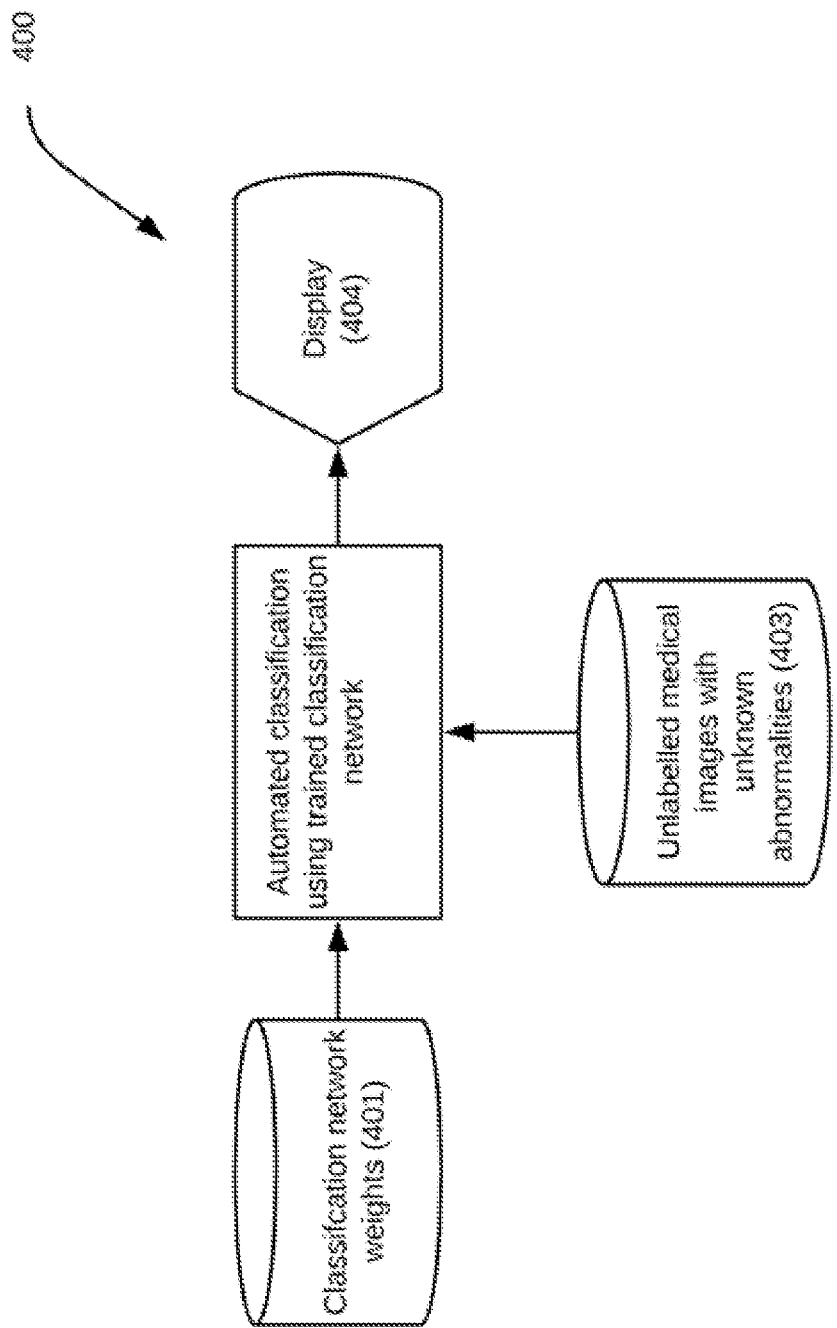
FIG. 6 shows an automated classification of images with unknown abnormalities.

FIG. 6 shows automated classification of images with unknown abnormalities.

Medical images with unknown abnormalities (403) can be used as input to the trained classification network. Weights of the classification network can be loaded from a storage device, such as a hard disk or solid-state drive (401). Normalization can be performed on images to ensure that an unlabeled image matches the statistics of the training dataset. Normalization may include any or all of: resizing to a certain image size, applying intensity normalization, or enhancing contrast of certain parts of the images where structures are difficult to delineate. Final classification results can be displayed to the user on a computer display (404).

Automated Segmentation of Images with Unknown Abnormalities (500)

Figure 7:
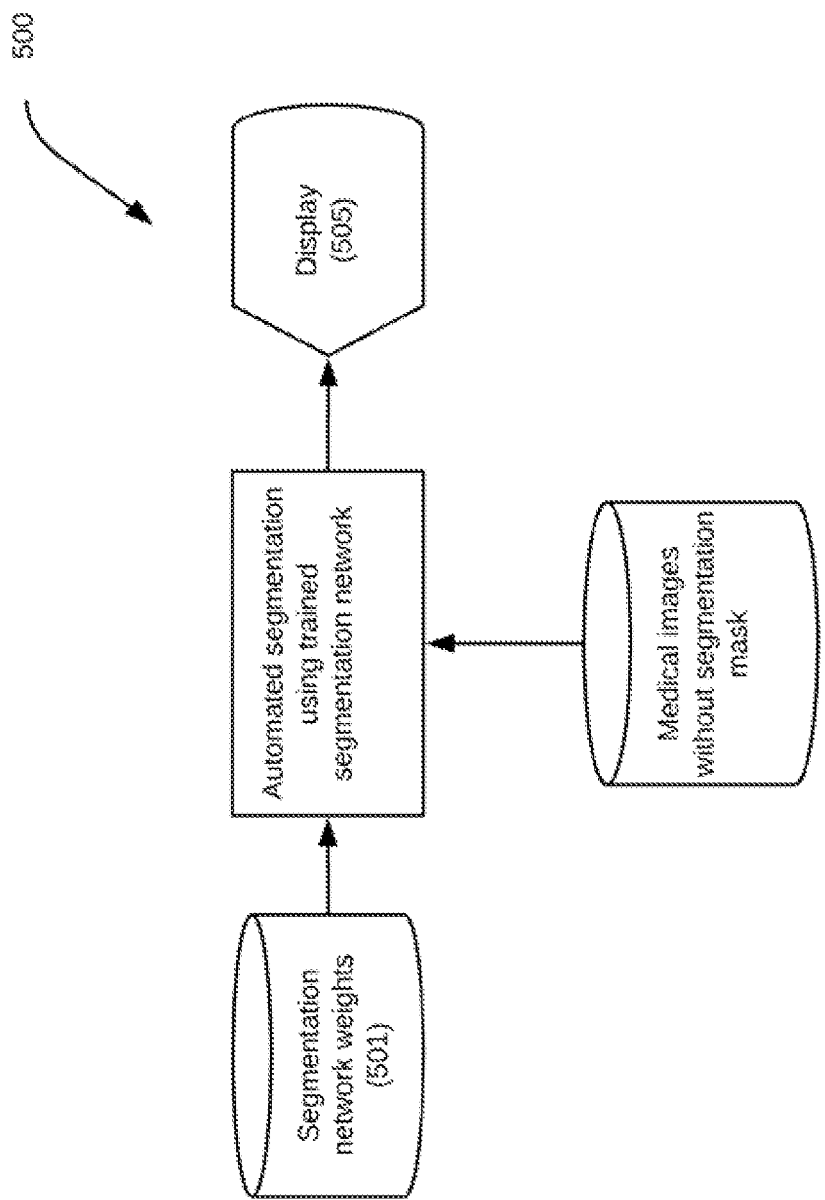
FIG. 7 shows an automated segmentation of images with unknown abnormalities.

FIG. 7 shows automated segmentation of images with unknown abnormalities.

Medical images with unknown abnormalities (501) can be used as input to the trained segmentation network. Weights of the classification network can be loaded from a storage device, such as a hard disk or solid-state drive (501). Normalization can be performed on images such that an unlabeled image matches the statistics of the training dataset. Normalization may include any or all of: resizing to a certain image size, applying intensity normalization, or enhancing contrast of certain parts of the images with structures are difficult to be delineated, for example. Final segmentation results can be displayed to the user on a computer display (505).

Example Computing Environment

Figure 8:
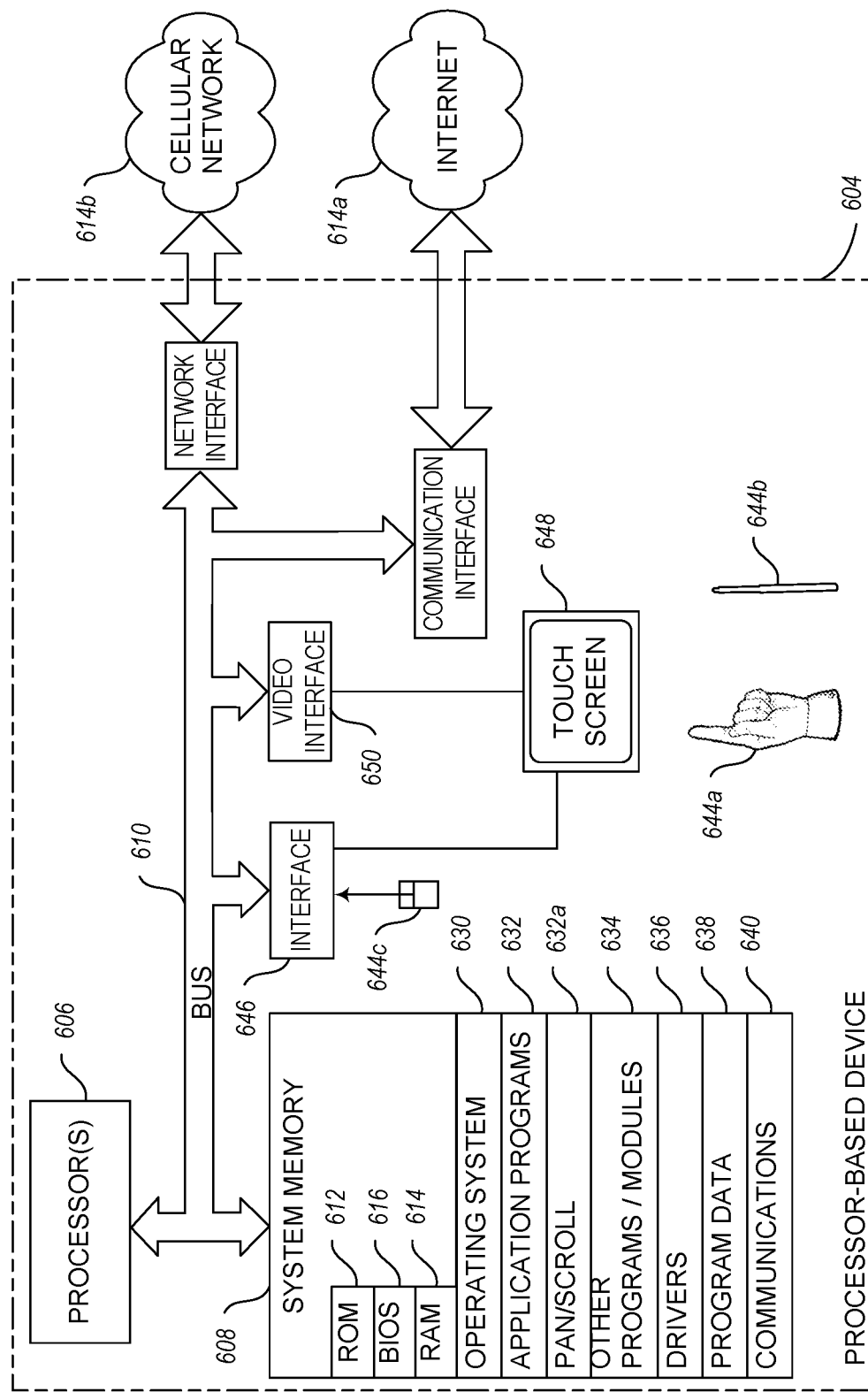
FIG. 8 shows an example computing environment for one or more implementations of the present disclosure.

FIG. 8 shows a processor-based device 604 suitable for implementing the various functionality described herein. Although not required, some portion of the implementations will be described in the general context of processor-executable instructions or logic, such as program application modules, objects, or macros being executed by one or more processors. Those skilled in the relevant art will appreciate that the described implementations, as well as other implementations, can be practiced with various processor-based system configurations, including handheld devices, such as smartphones and tablet computers, wearable devices, multiprocessor systems, microprocessor-based or programmable consumer electronics, personal computers ("PCs"), network PCs, minicomputers, mainframe computers, and the like.

The processor-based device 604 may include one or more processors 606, a system memory 608 and a system bus 610 that couples various system components including the system memory 608 to the processor(s) 606. The processor-based device 604 will at times be referred to in the singular herein, but this is not intended to limit the implementations to a single system, since in certain implementations, there will be more than one system or other networked computing device involved. Non-limiting examples of commercially available systems include, but are not limited to, ARM processors from a variety of manufactures, Core microprocessors from Intel Corporation, U.S.A., PowerPC microprocessor from IBM, Sparc microprocessors from Sun Microsystems, Inc., PA-RISC series microprocessors from Hewlett-Packard Company, 68xxx series microprocessors from Motorola Corporation.

The processor(s) 606 may be any logic processing unit, such as one or more central processing units (CPUs), microprocessors, digital signal processors (DSPs), application-specific integrated circuits (ASICs), field programmable gate arrays (FPGAs), etc. Unless described otherwise, the construction and operation of the various blocks shown in FIG. 8 are of conventional design. As a result, such blocks need not be described in further detail herein, as they will be understood by those skilled in the relevant art.

The system bus 610 can employ any known bus structures or architectures, including a memory bus with memory controller, a peripheral bus, and a local bus. The system memory 608 includes read-only memory ("ROM") 1012 and random access memory ("RAM") 614. A basic input/output system ("BIOS") 616, which can form part of the ROM 612, contains basic routines that help transfer information between elements within processor-based device 604, such as during start-up. Some implementations may employ separate buses for data, instructions and power.

The processor-based device 604 may also include one or more solid state memories, for instance Flash memory or solid state drive (SSD) 618, which provides nonvolatile storage of computer-readable instructions, data structures, program modules and other data for the processor-based device 604. Although not depicted, the processor-based device 604 can employ other nontransitory computer- or processor-readable media, for example a hard disk drive, an optical disk drive, or memory card media drive.

Program modules can be stored in the system memory 608, such as an operating system 630, one or more application programs 632, other programs or modules 634, drivers 636 and program data 638.

The application programs 632 may, for example, include panning/scrolling 632a. Such panning/scrolling logic may include, but is not limited to logic that determines when and/or where a pointer (e.g., finger, stylus, cursor) enters a user interface element that includes a region having a central portion and at least one margin. Such panning/scrolling logic may include, but is not limited to logic that determines a direction and a rate at which at least one element of the user interface element should appear to move, and causes updating of a display to cause the at least one element to appear to move in the determined direction at the determined rate. The panning/scrolling logic 632a may, for example, be stored as one or more executable instructions. The panning/scrolling logic 632a may include processor and/or machine executable logic or instructions to generate user interface objects using data that characterizes movement of a pointer, for example data from a touch-sensitive display or from a computer mouse or trackball, or other user interface device.

The system memory 608 may also include communications programs 640, for example a server and/or a Web client or browser for permitting the processor-based device 604 to access and exchange data with other systems such as user computing systems, Web sites on the Internet, corporate intranets, or other networks as described below. The communications programs 640 in the depicted implementation is markup language based, such as Hypertext Markup Language (HTML), Extensible Markup Language (XML) or Wireless Markup Language (WML), and operates with markup languages that use syntactically delimited characters added to the data of a document to represent the structure of the document. A number of servers and/or Web clients or browsers are commercially available such as those from Mozilla Corporation of California and Microsoft of Washington.

While shown in FIG. 8 as being stored in the system memory 608, the operating system 630, application programs 632, other programs/modules 634, drivers 636, program data 638 and server and/or browser 640 can be stored on any other of a large variety of nontransitory processor-readable media (e.g., hard disk drive, optical disk drive, SSD and/or flash memory).

A user can enter commands and information via a pointer, for example through input devices such as a touch screen 648 via a finger 644a, stylus 644b, or via a computer mouse or trackball 644c which controls a cursor. Other input devices can include a microphone, joystick, game pad, tablet, scanner, biometric scanning device, etc. These and other input devices (i.e., "I/O devices") are connected to the processor(s) 606 through an interface 646 such as touch-screen controller and/or a universal serial bus ("USB") interface that couples user input to the system bus 610, although other interfaces such as a parallel port, a game port or a wireless interface or a serial port may be used. The touch screen 648 can be coupled to the system bus 610 via a video interface 650, such as a video adapter to receive image data or image information for display via the touch screen 648. Although not shown, the processor-based device 604 can include other output devices, such as speakers, vibrator, haptic actuator, etc.

The processor-based device 604 may operate in a networked environment using one or more of the logical connections to communicate with one or more remote computers, servers and/or devices via one or more communications channels, for example, one or more networks 614a, 614b. These logical connections may facilitate any known method of permitting computers to communicate, such as through one or more LANs and/or WANs, such as the Internet, and/or cellular communications networks. Such networking environments are well known in wired and wireless enterprise-wide computer networks, intranets, extranets, the Internet, and other types of communication networks including telecommunications networks, cellular networks, paging networks, and other mobile networks.

When used in a networking environment, the processor-based device 604 may include one or more wired or wireless communications interfaces 614a, 614b (e.g., cellular radios, WI-FI radios, Bluetooth radios) for establishing communications over the network, for instance the Internet 614a or cellular network.

In a networked environment, program modules, application programs, or data, or portions thereof, can be stored in a server computing system (not shown). Those skilled in the relevant art will recognize that the network connections shown in FIG. 8 are only some examples of ways of establishing communications between computers, and other connections may be used, including wirelessly.

For convenience, the processor(s) 606, system memory 608, network and communications interfaces 614a, 614b are illustrated as communicably coupled to each other via the system bus 610, thereby providing connectivity between the above-described components. In alternative implementations of the processor-based device 604, the above-described components may be communicably coupled in a different manner than illustrated in FIG. 8. For example, one or more of the above-described components may be directly coupled to other components, or may be coupled to each other, via intermediary components (not shown). In some implementations, system bus 610 is omitted and the components are coupled directly to each other using suitable connections.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Those of skill in the art will recognize that many of the methods or algorithms set out herein may employ additional acts, may omit some acts, and/or may execute acts in a different order than specified.

In addition, those skilled in the art will appreciate that the mechanisms taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/571,908 filed Jul. 7, 2011; U.S. Pat. No. 9,513,357 issued Dec. 6, 2016; U.S. patent application Ser. No. 15/363,683 filed Nov. 29, 2016; U.S. Provisional Patent Application No. 61/928,702 filed Jan. 17, 2014; U.S. patent application Ser. No. 15/112,130 filed Jul. 15, 2016; U.S. Provisional Patent Application No. 62/260,565 filed Nov. 20, 2015; 62/415,203 filed Oct. 31, 2016; U.S. Provisional Patent Application No. 62/415,666 filed Nov. 1, 2016; U.S. Provisional Patent Application No. 62/451,482 filed Jan. 27, 2017; U.S. Provisional Patent Application No. 62/501,613 filed May 4, 2017; U.S. Provisional Patent Application No. 62/512,610 filed May 30, 2017; U.S. patent application Ser. No. 15/879,732 filed Jan. 25, 2018; U.S. patent application Ser. No. 15/879,742 filed Jan. 25, 2018; U.S. Provisional Patent Application No. 62/589,825 filed Nov. 22, 2017; U.S. Provisional Patent Application No. 62/589,805 filed Nov. 22, 2017; U.S. Provisional Patent Application No. 62/589,772 filed Nov. 22, 2017; U.S. Provisional Patent Application No. 62/589,872 filed Nov. 22, 2017; U.S. Provisional Patent Application No. 62/589,876 filed Nov. 22, 2017; U.S. Provisional Patent Application No. 62/589,766 filed Nov. 22, 2017; U.S. Provisional Patent Application No. 62/589,833 filed Nov. 22, 2017; U.S. Provisional Patent Application No. 62/589,838 filed Nov. 22, 2017; PCT Application No. PCT/US2018/015222 filed Jan. 25, 2018; PCT Application No. PCT/US2018/030963 filed May 3, 2018; U.S. patent application Ser. No. 15/779,445 filed May 25, 2018; U.S. patent application Ser. No. 15/779,447 filed May 25, 2018; U.S. patent application Ser. No. 15/779,448 filed May 25, 2018, PCT Application No. PCT/US2018/035192 filed May 30, 2018, and U.S. Provisional Patent Application No. 62/683,461 filed Jun. 11, 2018, are incorporated herein by reference, in their entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

[1] Esteva, Andre, Brett Kuprel, Roberto A. Novoa, Justin Ko, Susan M. Swetter, Helen M. Blau, and Sebastian Thrun. 2017. "Dermatologist-Level Classification of Skin Cancer with Deep Neural Networks." Nature 542 (7639): 115-18.

[2] Goodfellow, Ian J., Jean Pouget-Abadie, Mehdi Mirza, Bing Xu, David Warde-Farley, Sherjil Ozair, Aaron Courville, and Yoshua Bengio. 2014. "Generative Adversarial Networks." arXiv [stat.ML]. arXiv. http://arxiv.org/abs/1406.2661.

[3] Radford, Alec, Luke Metz, and Soumith Chintala 2015. "Unsupervised Representation Learning with Deep Convolutional Generative Adversarial Networks." arXiv [cs.LG]. arXiv. http://arxiv.org/abs/1511.06434.

[4] Isola, Phillip, Jun-Yan Zhu, Tinghui Zhou, and Alexei A. Efros. 2016. "Image-to-Image Translation with Conditional Adversarial Networks." arXiv [cs.CV]. arXiv. http://arxiv.org/abs/1611.07004.

[5] Mao, Xudong, Qing Li, Haomn Xie, Raymond Y. K. Lau, Zhen Wang, and Stephen Paul Smolley. 2016. "Least Squares Generative Adversarial Networks." arXiv [cs.CV]. arXiv. http://arxiv.org/abs/1611.04076.

[6] Sixt, Leon, Benjamin Wild, and Tim Landgraf. 2016. "RenderGAN: Generating Realistic Labeled Data." arXiv [cs.NE]. arXiv. http://arxiv.org/abs/1611.01331.

[7] Shrivastava, Ashish, Tomas Pfister, Oncel Tuzel, Josh Susskind, Wenda Wang, and Russ Webb. 2016. "Learning from Simulated and Unsupervised Images through Adversarial Training." arXiv [cs.CV]. arXiv. http://arxiv.org/abs/1612.07828.

[8] Manam, Giovanni, Florian Scheidegger, Roxana Istrate, Costas Bekas, and Cristiano Malossi. 2018. "BAGAN: Data Augmentation with Balancing GAN." arXiv [cs.CV]. arXiv. http://arxiv.org/abs/1803.09655.

[9] Mirza, Mehdi, and Simon Osindero. 2014. "Conditional Generative Adversarial Nets." arXiv [cs.LG]. arXiv. http://arxiv.org/abs/1411.1784.

[10] Odena, Augustus, Christopher Olah, and Jonathon Shlens. 2016. "Conditional Image Synthesis With Auxiliary Classifier GANs." arXiv [stat.ML]. arXiv. http://arxiv.org/abs/1610.09585.

[11] Costa, Pedro, Adrian Galdran, Maria Ines Meyer, Michael David Abramoff, Meindert Niemeijer, Ana Maria Mendonca, and Aurelio Campilho. 2017. "Towards Adversarial Retinal Image Synthesis." arXiv [cs.CV], January. https://arxiv.org/abs/1701.08974.

[12] Zhao, He, Huiqi Li, and Li Cheng. 2017. "Synthesizing Filamentary Structured Images with GANs." arXiv [cs.CV]. arXiv. http://arxiv.org/abs/1706.02185.

[13] Baur, Christoph, Shadi Albarqouni, and Nassir Navab. 2018. "MelanoGANs: High Resolution Skin Lesion Synthesis with GANs." arXiv [cs.CV]. arXiv. http://arxiv.org/abs/1804.04338.

[14] Frid-Adar, Maayan, Idit Diamant, Eyal Klang, Michal Amitai, Jacob Goldberger, and Hayit Greenspan. 2018. "GAN-Based Synthetic Medical Image Augmentation for Increased CNN Performance in Liver Lesion Classification." arXiv [cs.CV]. arXiv. http://arxiv.org/abs/1803.01229.

[15] Chuquicusma, M. J. M., S. Hussein, J. Burt, and U. Bagci. 2018. "How to Fool Radiologists with Generative Adversarial Networks? A Visual Turing Test for Lung Cancer Diagnosis." In 2018 IEEE 15th International Symposium on Biomedical Imaging (ISBI 2018), 240-44.

[16] Zhu, Jun-Yan, Taesung Park, Phillip Isola, and Alexei A. Efros. 2017. "Unpaired Image-to-Image Translation Using Cycle-Consistent Adversarial Networks." arXiv [cs.CV]. arXiv. http://arxiv.org/abs/1703.10593.

[17] Wolterink, Jelmer M., Anna M. Dinkla, Mark H. F. Savenije, Peter R. Seevinck, Cornelis A. T. van den Berg, and Ivan. Isgum. 2017. "Deep MR to CT Synthesis Using Unpaired Data." *arXiv* [cs.CV]. arXiv. http://arxiv.org/abs/1708.01155.

[18] Salehinejad, Hojjat, Shahrokh Valaee, Tim Dowdell, Errol Colak, and Joseph Barfett. 2017. "Generalization of Deep Neural Networks for Chest Pathology Classification in X-Rays Using Generative Adversarial Networks." *arXiv* [cs.CV]. arXiv. http://arxiv.org/abs/1712.01636.

[19] Kingma, Diederik, and Jimmy Ba. 2014. "Adam: A Method for Stochastic Optimization" *arXiv* [cs.LG]. arXiv. http://arxiv.org/abs/1412.6980.

[20] Schulz-Menger, Jeanette, David A. Bluemke, Jens Bremerich, Scott D. Flamm, Mark A. Fogel, Matthias G Friedrich, Raymond J. Kim, et al. 2013. "Standardized Image Interpretation and Post Processing in Cardiovascular Magnetic Resonance: Society for Cardiovascular Magnetic Resonance (SCMR) Board of Trustees Task Force on Standardized Post Processing." *Journal of Cardiovascular Magnetic Resonance: Official Journal of the Society for Cardiovascular Magnetic Resonance* 15 (May): 35.

The invention claimed is:

1. A machine learning system, comprising:
one or more nontransitory processor-readable storage media that collectively store at least one of processor-executable instructions or data; and
one or more processors communicably coupled to the one or more nontransitory processor-readable storage media, wherein in operation, the one or more processors individually or collectively:
receives learning data comprising a plurality of batches of labeled image sets and corresponding segmentation masks, each image set comprising image data representative of an input anatomical structure;
simulates abnormalities on at least some images in the image sets and their corresponding segmentation masks without abnormalities, using a plurality of trained convolutional neural network (CNN) models stored on the at least one nontransitory processor-readable storage medium, wherein the abnormalities are in at least one of (a) cardiac images, and include one or more of myocardial scarring, myocardial infarction, coronary stenosis, or perfusion characteristics of the cardiac myocardium, (b) lung images, and include one or more of ground glass, solid lung nodules, or sub-solid lung nodules, or (c) liver images, and include one or more of Hemangiomas, Focal Nodular Hyperplasias lesions, Hepatocellualar Adenomas lesions, or cystic masses; and
stores the simulated abnormalities as images and corresponding segmentation masks in the at least one nontransitory processor-readable storage medium of the machine learning system.

2. The machine learning system of claim 1 wherein at least some of the images include abnormalities comprising the simulated abnormalities or real abnormalities.

3. The machine learning system of claim 1 wherein the image data is representative of a chest, including lungs and heart, or of an abdomen, including a liver.

4. The machine learning system of claim 1 wherein the image data includes computed tomography (CT) scan data or magnetic resonance (MR) scan data.

5. The machine learning system of claim 1 wherein the image data is captured at any of a plurality of acquisition angles including short-axis of the heart, long-axis of the heart, axially, sagittally, or coronally.

6. A machine learning system, comprising:
one or more nontransitory processor-readable storage media that collectively store at least one of processor-executable instructions or data; and
one or more processors communicably coupled to the one or more nontransitory processor-readable storage media, wherein in operation, the one or more processors individually or collectively:
receives learning data comprising a plurality of batches of labeled image sets and corresponding segmentation masks, each image set comprising image data representative of an input anatomical structure;
simulates abnormalities on at least some images in the image sets and their corresponding segmentation masks without abnormalities, using a plurality of trained convolutional neural network (CNN) models stored on the at least one nontransitory processor-readable storage medium, wherein the CNN models include a discriminator which receives learning data comprising a plurality of batches of real samples and simulated samples and classifies if the samples contain real abnormalities, simulated abnormalities or no abnormalities and wherein the simulated samples include past simulated samples from a refining generator or a mask generator; and
stores the simulated abnormalities as images and corresponding segmentation masks in the at least one nontransitory processor-readable storage medium of the machine learning system.

7. The machine learning system of claim 6 wherein the discriminator is a mask discriminator, and the learning data includes segmentation masks with real abnormalities and segmentation masks with simulated abnormalities from a mask generator.

8. The machine learning system of claim 6 wherein the discriminator is a refining discriminator, and the learning data includes images without abnormalities and images with simulated abnormalities from a refining generator.

9. The machine learning system of claim 6 wherein at least one storage device with a fixed capacity stores past simulated images and segmentation masks from the mask generator and the refining generator.

10. The machine learning system of claim 9 wherein if the storage device is out of capacity, at least one random simulated image or segmentation mask is removed to accommodate new inputs.

11. The machine learning system of claim 6 wherein the CNN models include a discriminator comprising at least one group of layers that includes at least one convolution layer, max pooling layer, batch normalization layer and dropout layer where a nonlinearity including rectifier or leaky rectifier is applied after each multiplication, wherein there are more than one residual connection and skip connection among the group, and one output layer that includes at least one neuron.

12. The machine learning system of claim 11 wherein the output layer contains at least one neuron with a nonlinearity applied.

13. The machine learning system of claim 12 wherein the nonlinearity comprises softmax.

14. The machine learning system of claim 6 wherein the CNN models include a discriminator that is optimized using stochastic gradient descent using at least one differentiable objective function that is indicative of the accuracy of the discriminator.

15. The machine learning system of claim 14 wherein a differentiable objective function includes a combination of mean squared error, categorical cross-entropy or Wasserstein distance.

16. The machine learning system of claim 14 wherein a differentiable objective function includes a classification loss including categorical cross-entropy between the predicted and ground truth abnormality features.

17. A machine learning system, comprising:
one or more nontransitory processor-readable storage media that collectively store at least one of processor-executable instructions or data; and
one or more processors communicably coupled to the one or more nontransitory processor-readable storage media, wherein in operation, the one or more processors individually or collectively:
receives learning data comprising a plurality of batches of labeled image sets and corresponding segmentation masks, each image set comprising image data representative of an input anatomical structure;
simulates abnormalities on at least some images in the image sets and their corresponding segmentation masks without abnormalities, using a plurality of trained convolutional neural network (CNN) models stored on the at least one nontransitory processor-readable storage medium, wherein the CNN models include a mask discriminator and a mask generator, and the mask generator which receives learning data comprising a plurality of batches of real segmentation masks to add simulated abnormal tissues to the segmentation masks; and
stores the simulated abnormalities as images and corresponding segmentation masks in the at least one nontransitory processor-readable storage medium of the machine learning system.

18. The machine learning system of claim 17 wherein the mask generator comprises a contracting path and an expanding path, the contracting path includes a number of convolutional layers and a number of pooling layers, each pooling layer preceded by at least one convolutional layer, and the expanding path includes a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation.

19. The machine learning system of claim 17 wherein the CNN models include a mask discriminator and a mask generator, and the mask generator and the mask discriminator are optimized together with stochastic gradient descent such that the simulated segmentation mask generated by the mask generator maximizes the error of the mask discriminator and minimizes the differences between the input and output segmentation masks using at least one differentiable objective functions.

20. The machine learning system of claim 19 wherein the differentiable objective function that maximizes the error of the mask discriminator includes at least mean squared error or Wasserstein distance.

21. The machine learning system of claim 19 wherein the differentiable objective function that minimizes the differences between the input and output images includes at least one of mean absolute error, mean squared error, or categorical cross-entropy.

22. The machine learning system of claim 19 wherein the mask generator is optimized for N gradient steps and the mask discriminator is optimized for M gradients steps, where N and M are positive integers.

23. The machine learning system of claim 22 wherein N and M are different positive integers.

24. The machine learning system of claim 22 wherein N and M are equal to each other.

25. The machine learning system of claim 17 wherein the at least one processor applies the simulated segmentation mask with simulated abnormalities to the images by changing the intensity values of the corresponding pixels which belong to the simulated abnormalities.

26. The machine learning system of claim 25 wherein the at least one processor calculates the average intensity of abnormalities in the learning data and applies the calculated average intensity to the image to the pixels of the image which belong to the simulated abnormalities.

27. The machine learning system of claim 25 wherein the at least one processor uniformly samples from anatomical structures in the image and applies the sampled intensities of the image to the pixels of the image which belong to the simulated abnormalities.

28. The machine learning system of claim 27 wherein anatomical structures that the at least one processor sampled from include the left endocardium of heart images.

29. A machine learning system, comprising:
one or more nontransitory processor-readable storage media that collectively store at least one of processor-executable instructions or data; and
one or more processors communicably coupled to the one or more nontransitory processor-readable storage media, wherein in operation, the one or more processors individually or collectively:
receives learning data comprising a plurality of batches of labeled image sets and corresponding segmentation masks, each image set comprising image data representative of an input anatomical structure;
simulates abnormalities on at least some images in the image sets and their corresponding segmentation masks without abnormalities, using a plurality of trained convolutional neural network (CNN) models stored on the at least one nontransitory processor-readable storage medium, wherein the CNN models include a mask generator, a mask discriminator, and a refining generator, and the refining generator receives learning data comprising a plurality of batches of real images, segmentation masks with simulated abnormalities from the mask generator, and produces simulated abnormalities on the image using the received learning data; and
stores the simulated abnormalities as images and corresponding segmentation masks in the at least one nontransitory processor-readable storage medium of the machine learning system.

30. The machine learning system of claim 29 wherein the refining generator comprises a contracting path and an expanding path, the contracting path includes a number of convolutional layers and a number of pooling layers, each pooling layer preceded by at least one convolutional layer, and the expanding path includes a number of convolutional layers and a number of upsampling layers, each upsampling layer preceded by at least one convolutional layer and comprises a transpose convolution operation which performs at least one of an upsampling operation and an interpolation operation with a learned kernel, or an upsampling operation followed by an interpolation operation.

31. The machine learning system of claim 29 wherein the CNN models include a refining discriminator, and the refining generator and the refining discriminator are optimized together with stochastic gradient descent using at least one differentiable objective function such that the refining generator maximizes the error of the refining discriminator and minimizes the differences between the input and output images.

32. The machine learning system of claim 31 wherein the differentiable objective function that maximizes the error of the refining discriminator includes a combination of mean squared error or categorical cross-entropy.

33. The machine learning system of claim 31 wherein the differentiable objective function that minimizes the differences between the input and output image includes at least one of mean absolute error or mean squared error.

34. The machine learning system of claim 31 wherein the mask generator is optimized for N gradient steps and the mask discriminator is optimized for M gradients steps where N and M are positive integers.

35. The machine learning system of claim 34 wherein N and M are different positive integers.

36. The machine learning system of claim 34 wherein N and M are equal to each other.

\* \* \* \* \*